United States Patent [19]

Mardis et al.

[11] 4,434,075
[45] Feb. 28, 1984

[54] ANIONICALLY MODIFIED ORGANOPHILIC CLAYS AND THEIR PREPARATION

[75] Inventors: Wilbur S. Mardis, Trenton, N.J.; Claude M. Finlayson, Houston, Tex.

[73] Assignee: NL Industries, Inc., New York, N.Y.

[21] Appl. No.: 313,033

[22] Filed: Oct. 19, 1981

[51] Int. Cl.³ ............................................. B01J 13/00
[52] U.S. Cl. .................................. 252/315.2; 106/27; 106/38.7; 106/287.17; 252/8.5 M; 252/8.55 R; 252/28; 252/DIG. 8; 260/448 C; 524/236
[58] Field of Search ................... 260/448 C; 252/316, 252/28, 315.2; 106/287.17

[56] References Cited

U.S. PATENT DOCUMENTS

| | | | |
|---|---|---|---|
| 2,033,856 | 3/1936 | Smith | 546/10 |
| 2,531,427 | 11/1950 | Hauser | 260/448 C |
| 2,531,440 | 11/1950 | Jordan | 252/28 |
| 2,548,679 | 4/1951 | Olin | 564/285 |
| 2,658,869 | 11/1953 | Stross et al. | 252/28 |
| 2,767,177 | 10/1956 | Erickson | 260/242 |
| 2,859,234 | 11/1958 | Clem | 252/34 X |
| 3,461,163 | 8/1969 | Boothe | 564/296 |
| 3,472,740 | 10/1969 | Boothe | 203/37 |
| 3,537,994 | 11/1970 | House | 252/13 |
| 3,929,849 | 12/1975 | Oswald | 260/448 C |
| 3,945,836 | 3/1976 | Miyata | 106/22 |
| 3,974,125 | 8/1976 | Oswald et al. | 523/216 |
| 4,054,537 | 10/1977 | Wright et al. | 423/331 |
| 4,097,437 | 6/1978 | Dhake | 524/236 |
| 4,116,866 | 9/1978 | Finlayson | 252/315.2 |
| 4,317,737 | 3/1982 | Oswald et al. | 252/28 |

FOREIGN PATENT DOCUMENTS 1106281 3/1968 United Kingdom ................ 252/316
1592271 7/1981 United Kingdom .

OTHER PUBLICATIONS

The Condensed Chemical Dictionary, 9th Edition, Revised by Hawley, Van Nostrand Reinhold Co. (1977), p. 636.
H. Van Olphen: "An Introduction to Clay Colloid Chemistry", 2nd Edition, John Wiley & Sons, New York, London, Sydney, Toronto (1963), p. 64.
"Industrial Minerals and Rocks", 4th Ed., S. J. Lefond, Ed., American Institute of Mining, Metallurgical, and Petroleum Engineers, Inc., New York, N.Y. (1975), pp. 1244–1247.
R. E. Grim: "Clay Mineralogy", 2nd Ed., McGraw Hill Book Co., New York, St. Louis, San Francisco, Toronto, London, Sydney (1968), pp. 77–79.

*Primary Examiner*—Richard D. Lovering

[57] ABSTRACT

An organophilic clay gellant is disclosed which comprises the reaction product of an organic cation compound, an organic anion, and a smectite-type clay having a cation exchange capacity of at least 75 milliequivalents per 100 grams of said clay. The organic cation compound has the formula:

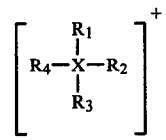

wherein $R_1$ is selected from the group consisting of a $\beta$, $\gamma$-unsaturated alkyl group and a hydroxyalkyl group having 2 to 6 carbon atoms and mixtures thereof; $R_2$ is a long chain alkyl group having 12 to 60 carbon atoms; $R_3$ and $R_4$ are individually selected from the group consisting of a $\beta$, $\gamma$-unsaturated alkyl group, a hydroxyalkyl group having 2 to 6 carbon atoms, an aralkyl group, an alkyl group having from 1 to 22 carbon atoms and mixtures thereof; X is selected from a group consisting of phosphorous and nitrogen. The reaction is carried out in a manner such that an organic cation-organic anion complex is intercalated with the smectite-type clay and the cation exchange sites of the smectite-type clay are substituted with the organic cation.

17 Claims, No Drawings

ANIONICALLY MODIFIED ORGANOPHILIC CLAYS AND THEIR PREPARATION

This invention relates to organophilic organic-clay complexes which are dispersible in organic liquids to form a gel therein. Depending on the composition of the gel, such gels may be useful as lubricating greases, oil base muds, oil base packer fluids, paint-varnish-lacquer removers, paints, foundry molding sand binders, adhesives and sealants, inks, polyester laminating resins, polyester gel coats, and the like.

It is well known that organic compounds which contain a cation will react under favorable conditions by ion-exchange with clays which contain a negative layer-lattice and exchangeable cations to form organophilic organic-clay products. If the organic cation contains at least one alkyl group containing at least 10 carbon atoms, then such organoclays have the property of swelling in certain organic liquids. See for Example U.S. Pat. No. 2,531,427 and U.S. Pat. No. 2,966,506, both incorporated herein by reference, and the book "Clay Mineralogy", 2nd Edition, 1968 by Ralph E. Grim (McGraw-Hill Book Company, Inc.), particularly Chapter 10, Clay-Mineral-Organic Reactions; pp. 356–368—Ionic Reactions, Smectite; and pp. 392–401—Organophilic Clay-Mineral Complexes.

It is also known that organic compounds presented in the anionic form are usually repelled by, rather than attracted to, the negatively charged clay surface. This effect is referred to as negative adsorption. However, positive adsorption of anions can occur under conditions in which such compounds exist in the molecular, i.e., undissociated form. See "Chemistry of Clay—Organic Reactions" 1974 by B. K. G. Theng, John Wiley & Sons.

In contrast, Wada found that this phenomena, i.e., adsorption, does occur with certain ionic compounds when reacted with halloysite, kaolinite group material, to form intersalates. Intersalation was achieved by grinding the mineral with moist crystals of salts of low molecular weight carboxylic acids or by contacting the mineral with saturated solutions. This interlayer complex contained the complete salt as well as water. The intersalated material however was removed by washing with water resulting in either hydration of the interlayer or collapse to the original spacing. No evidence of variation in basal spacing was found with montmorillonite treated with salts in contrast with halloysite. See *The American Minerologist*, Volume 44, 1959, by K. Wada "Oriented Penetration of Ionic Compounds between the Silicate Layers of Halloysite".

Since the commercial introduction of organoclays in the early 1950's, it has become well known that maximum gelling (thickening) efficiency from these organoclays is achieved by adding a low molecular weight polar organic material to the composition. Such polar organic materials have been variously called dispersants, dispersion aids, solvating agents, dispersion agents and the like. See for example the following U.S. patents: O'Halloran U.S. Pat. No. 2,677,661; McCarthy et al. U.S. Pat. No. 2,704,276; Stratton U.S. Pat. No. 2,833,720; Stratton U.S. Pat. No. 2,879,229; Stansfield et al. U.S. Pat. No. 3,294,683. The use of such dispersion aids was found unnecessary when using specially designed organophilic clays derived from substituted quaternary ammonium compounds. See U.S. patents: Finlayson et al. U.S. Pat. No. 4,105,578 and Finlayson U.S. Pat. No. 4,208,218.

In contrast to the prior art organoclay compositions, a self-activating rheological agent has been unexpectedly produced which does not require the addition of polar solvent activators, which agent is produced from the reaction of an organic cation, an organic anion and a smectite-type clay.

An organophilic clay gellant having enhanced dispersibility in non-aqueous systems has been unexpectedly discovered which comprises the reaction product of:

a. an organic cation salt compound, wherein said organic cation has the formula:

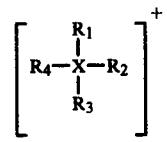

wherein $R_1$ is selected from the group consisting of a $\beta$, $\gamma$-unsaturated alkyl group and a hydroxyalkyl group having 2 to 6 carbon atoms and mixtures thereof; $R_2$ is a long chain alkyl group having 12 to 60 carbon atoms; $R_3$ and $R_4$ are individually selected from the group consisting of a $\beta$, $\gamma$-unsaturated alkyl group, a hydroxyalkyl group having 2 to 6 carbon atoms, an aralkyl group, an alkyl group having from 1 to 22 carbon atoms and mixtures thereof; X is selected from a group consisting of phosphorous and nitrogen;

b. an organic anion; and c. a smectite-type clay having a cation exchange capacity of at least 75 milliequivalents per 100 grams of said clay;

such that an organic cation—organic anion complex is intercalated with the smectite-type clay and the cation exchange sites of the smectite-type clay are substituted with the organic cation.

The organophilic clays of the invention may be prepared by admixing the organic anion with a clay and water together, preferably at a temperature between 20° C. and 100° C., preferably between 35° and 77° C. for a sufficient time to prepare a homogeneous mixture followed by the addition of the organic cation in sufficient amounts to satisfy the cation exchange capacity of the clay and the cationic capacity of the organic anion. The order of addition of the organic cation and organic anion is not significant as long as a sufficient amount of organic cation is added. In fact, the appropriate quantities of organic cation and sodium salt of the organic anion, in solution (water and/or 2-propanol) at a 20 to 90% solids basis, may be premixed to form an organic cation-organic anion complex and then added as a solution to react with the clay slurry. After addition of the organic anion and organic cation, the mixture is reacted with agitation at a temperature between 20° C. and 100° C., preferably between 35° and 77° C., for a sufficient time to allow the formation of an organic cation-organic anion complex which is intercalated with the clay and the cation exchange sites of the clay are substituted with the organic cation. Reaction temperatures below 20° C. or above 100° C., while usable, are not preferred.

The addition of the organic cation and organic anion may be done either separately or as a complex. In using the organophilic clays in emulsions, the drying and grinding steps may be eliminated. When the clay, organic cation, organic anion and water are mixed in such concentrations that a slurry is not formed, the filtration and washing steps can be eliminated.

The clay is preferably dispersed in water at a concentration from about 1 to 80% and preferably 2% to 7% to form a clay slurry. The clay slurry may be optionally centrifuged to remove non-clay impurities which constitute about 10% to about 50% of the starting clay composition. The slurry is generally pre-heated under agitation to a temperature in the range from 35° C. to 77° C. before the addition of the organic reactants.

The amount of organic anion added to the clay for purposes of this invention should be sufficient to impart to the organophilic clay the enhanced dispersion characteristic desired. This amount is defined as the milliequivalent ratio which is the number of milliequivalents (M.E.) of the organic anion in the organoclay per 100 grams of clay, 100% active clay basis. The organophilic clays of this invention should preferably have an anion milliequivalent ratio of 5 to 100 and more preferably 10 to 50.

The organic anion is preferably added to the reactants in the desired milliequivalent ratio as a solid or solution in water under agitation to effect a homogenous mixture.

The organic cation should be employed in a sufficient quantity to at least satisfy the cation exchange capacity of the clay and the cationic activity of the organic anion. Additional cation above the sum of the exchange capacity of the clay and anion may be optionally used. It has been found that use of at least 90 milliequivalents of organic cation is sufficient to satisfy a portion of the total organic cation requirement. Use of amounts from 80 to 200 M.E.—and preferably from 100 to 160 M.E. are acceptable.

For convenience of handling it is preferred that the total organic content of the organophilic clay reaction products of this invention should be less than about 50% by weight of the organoclay. Higher amounts are usable, but the reaction product is difficult to process.

Another process for preparing the organophilic clays of this invention comprises:

a. slurrying a smectite-type clay in water at 1 to 80% by weight of said clay;

b. heating the slurry to a temperature between 20° C. and 100° C.;

c. adding 5 to 100 milliequivalents of an organic anion per 100 grams of clay, 100% active clay basis and the organic cation in a sufficient amount to satisfy the cation exchange capacity of the smectite-type clay and the cationic activity of the organic anion while agitating the reaction solution;

d. reacting the mixture for a sufficient time to form a reaction product comprising an organic cation-organic anion complex which is intercalated with the smectite-type clay and the cation exchange sites of the smectite-type clay are substituted with the organic cation; and e. recovering the reaction product.

The organic cationic compounds useful in this invention may be selected from a wide range of materials that are capable of forming an organophilic clay by exchange of cations with the smectite-type clay. The organic cationic compound must have a positive charge localized on a single atom or on a small group of atoms within the compound. Preferably the organic cation is selected from the group consisting of quaternary ammonium salts, phosphonium salts, and mixtures thereof, as well as equivalent salts. The organic cation preferably contains at least one member selected from each of two groups, the first group consisting of (a) a $\beta$, $\gamma$-unsaturated alkyl group, and (b) a hydroxyalkyl group having 2 to 6 carbon atoms, and the second consisting of a long chain alkyl group. The remaining moieties on the central positive atom are chosen from a member from a $\beta$, $\gamma$-unsaturated alkyl group and/or a hydroxyalkyl group having 2 to 6 carbon atoms or an aralkyl group and/or an alkyl group having from 1 to 22 carbon atoms.

A representative formula of the cationic compound is:

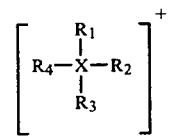

wherein $R_1$ is selected from the group consisting of a $\beta$, $\gamma$-unsaturated alkyl group and a hydroxyalkyl group having 2 to 6 carbon atoms; $R_2$ is a long chain alkyl group having 12 to 60 carbon atoms; $R_3$ and $R_4$ are selected from a group consisting of a $\beta$, $\gamma$-unsaturated alkyl group, a hydroxyalkyl group having 2 to 6 carbon atoms, an aralkyl group, and an alkyl group having from 1 to 22 carbon atoms; X is phosphorous or nitrogen.

$R_1$

The $\beta$, $\gamma$-unsaturated alkyl group may be selected from a wide range of materials. These compounds may be cyclic or acyclic, unsubstituted or substituted. $\beta$, $\gamma$-unsaturated alkyl radicals preferably contain less than 7 aliphatic carbon atoms. $\beta$, $\gamma$-unsaturated alkyl radicals substituted with an aliphatic radical preferably contains less than 4 aliphatic carbons. The $\beta$, $\gamma$-unsaturated alkyl radical may be substituted with an aromatic ring that likewise is conjugated with the unsaturation of the $\beta$, $\gamma$-moiety or the $\beta$, $\gamma$-radical is substituted with both an aliphatic radical and aromatic ring.

Representative examples of cyclic, $\beta$, $\gamma$-unsaturated alkyl groups include 2-cyclohexenyl and 2-cyclopentenyl. Representative examples of acyclic $\beta$, $\gamma$-unsaturated alkyl groups containing 6 or less carbon atoms include propargyl; 2-propenyl; 2-butenyl; 2-pentenyl; 2-hexenyl; 3-methyl-2-butenyl; 3-methyl-2-pentenyl; 2,3-dimethyl-2-butenyl; 1,1-dimethyl-2-propenyl; 1,2-dimethyl propenyl; 2,4-pentadienyl; and 2,4-hexadienyl. Representative examples of acyclic-aromatic substituted compounds include 3-phenyl-2-propenyl; 2-phenyl-2-propenyl and 3-(4-methoxyphenyl)-2-propenyl. Representative examples of aromatic and aliphatic substituted materials include 3-phenyl-2-cyclohexenyl; 3-phenyl-2-cyclopentenyl; and other similar groups.

The hydroxyalkyl group is selected from a hydroxyl substituted aliphatic radical wherein the hydroxyl is not substituted at the carbon adjacent to the positively charged atom and the group has from 2 to 6 aliphatic carbons. The alkyl group may be substituted with an aromatic ring. Representative examples include 2-hydroxyethyl; 3-hydroxypropyl; 4-hydroxypentyl; 6-hydroxyhexyl; 2-hydroxypropyl; 2-hydroxybutyl; 2-hydroxypentyl; 2-hydroxyhexyl; 2-hydroxycyclohexyl; 3-hydroxycyclohexy; 4-hydroxycyclohexyl; 2-hydroxycyclopentyl; 3-hydroxycyclopentyl; 2-methyl-2- hydroxypropyl; 3-methyl-2-hydroxybutyl; and 5-hydroxy-2-pentenyl.

$R_2$

The long chain alkyl radicals may be branched or unbranched, saturated or unsaturated, substituted or unsubstituted and should have from 12 to 60 carbon atoms in the straight chain portion of the radical.

The long chain alkyl radicals may be derived from natural occurring oils including various vegetable oils, such as corn oil, coconut oil, soybean oil, cottonseed oil, castor oil and the like, as well as various animal oils or fats such as tallow oil. The alkyl radicals may likewise be petrochemically derived such as from alpha olefins.

Representative examples of useful branched, saturated alkyl radicals include 12-methylstearyl; and 12-ethylstearyl. Representative examples of useful branched, unsaturated radicals include 12-methyloleyl and 12-ethyloleyl. Representative examples of unbranched saturated radicals include lauryl; stearyl; tridecyl; myristyl (tetradecyl); pentadecyl; hexadecyl; hydrogenated tallow, and docosonyl. Representative examples of unbranched, unsaturated and unsubstituted long chain alkyl radicals include oleyl, linoleyl; linolenyl, soya and tallow.

$R_3$ and $R_4$

The remaining groups on the positive charged atom are chosen from a group consisting of (a) a $\beta$, $\gamma$-unsaturated alkyl group (b) a hydroxyalkyl group having 2 to 6 carbon atoms, both described above; (c) an alkyl group having 1 to 22 carbon atoms, cyclic or acyclic and (d) an aralkyl group, that is benzyl and substituted benzyl moieties including fused ring moieties having linear or branched chains of 1 to 22 carbon atoms in the alkyl portion of the aralkyl.

The unsaturated alkyl group of $R_3$ and $R_4$ may be linear and branched, cyclic and acyclic, substituted and unsubstituted, containing 1 to 22 carbon atoms.

Representative examples of useful alkyl groups useful as $R_3$ and $R_4$ include methyl; ethyl; propyl; 2-propyl; iso-butyl; cyclopentyl; and cyclohexyl.

The alkyl radicals may be derived from a similar source as the long chain alkyl radical of $R_2$ above.

Representative examples of an aralkyl group, that is benzyl and substituted benzyl moieties, would include benzyl and those materials derived from, e.g. benzyl halides, benzhydryl halides, trityl halides, 1-halo-1-phenylalkanes wherein the alkyl chain has from 1 to 22 carbon atoms such as 1-halo-1-phenylethane; 1-halo-1-phenyl propane; and 1-halo-1-phenyloctadecane; substituted benzyl moieties such as would be derived from ortho-, meta- and para-chlorobenzyl halides, para-methoxybenzyl halides; ortho-, meta- and para-nitrilobenzyl halides, and ortho-, meta- and para-alkylbenzyl halides wherein the alkyl chain contains from 1 to 22 carbon atoms; and fused ring benzyl-type moieties such as would be derived from 2-halomethylnaphthalene, 9-halomethylanthracene and 9-halomethylphenanthrene, wherein the halo group would be defined as chloro-, bromo-, iodo-, or any other such group which serves as a leaving group in the nucleophilic attack of the benzyl type moiety such that the nucleophile replaces the leaving group on the benzyl type moiety.

A quaternary compound is formed of the above described organic cationic compound and an anionic radical which may be $Cl^-$, $Br^-$, $I^-$, $NO_2^-$, $OH^-$, and $C_2H_3O_2^-$ and mixtures thereof. Preferably the anion is selected from the group consisting of chloride and bromide, and mixtures thereof, and is more preferably chlorine, although other anions such as acetate, hydroxide, nitrite, etc., may be present in the organic cationic compound to neutralize the cation.

Organic cationic salts may be prepared by known methods as disclosed in U.S. Pat. Nos. 2,355,356, 2,775,617 and 3,136,819.

The organic anions useful in this invention may be selected from a wide range of materials providing they are capable of reacting with an organic cation and form intercalations with a smectite-type clay as an organic cation-organic anion complex. The molecular weight (gram molecular weight) of the organic anion is preferably 3,000 or less, and more preferably 1,000 or less, and contains at least one acidic moiety per molecule as disclosed herein. The organic anion is preferably derived from an organic acid having a $pK_A$ less than about 11.0. As indicated, the source acid must contain at least one ionizable hydrogen having the preferred $pK_A$ in order to allow the formation of the organic cation-organic intercalation reaction to occur.

Also usable is any compound which will provide the desired organic anion on hydrolysis. Representative compounds include:

(1) acid anhydrides including acetic anhydride, maleic anhydride, succinic anhydride and phthalic anhydride;

(2) acid halides including acetyl chloride, octanoyl chloride, lauroyl chloride, lauroyl bromide and benzoyl bromide;

(3) 1,1,1-trihalides including 1,1,1-trichloroethane and 1,1,1-tribromooctane; and (4) orthoesters including ethylorthoformate and ethylorthostearate.

The organic anions may be in the acid or salt form. Salts may be selected from alkali metal salts, alkaline earth salts, ammonia, and organic amines. Representative salts include: hydrogen, lithium, sodium, potassium, magnesium, calcium, barium, ammonium and organic amines such as ethanolamine, diethanolamine, triethanolamine, methyl diethanolamine, butyl diethanolamine, diethyl amine, dimethyl amine, triethyl amine, dibutyl amine, and so forth, and mixtures thereof. The most preferred salt is sodium as the alkali metal salt.

Exemplary types of suitable acidic functional organic compounds useful in this invention include:

(1) Carboxylic acids including:

(a) benzene carboxylic acids such as benzoic acid, ortho-, meta- and para-phthalic acid, 1,2,3-benzenetricarboxylic acid; 1,2,4-benzenetricarboxylic acid, 1,3,5-benzenetricarboxylic acid; 1,2,4,5-benzenetetracarboxylic acid; 1,2,3,4,5,6-benzenehexacarboxylic acid (mellitic acid);

(b) alkyl carboxylic acids having the formula H—$(CH_2)_n$—COOH, wherein n is a number from 0 to 20, such compounds include acetic acid; propionic acid; butanoic acid; pentanoic acid; hexanoic acid; heptanoic acid; octanoic acid; nonanoic acid; decanoic acid; undecanoic acid; lauric acid; tridecanoic acid; tetradecanoic acid; pentadecanoic acid; hexadecanoic acid; heptadecanoic acid; octadecanoic acid (stearic acid); nonadecanoic acid; eicosonic acid;

(c) alkyl dicarboxylic acids having the formula HOOC—$(CH_2)_n$—COOH, wherein n is 0 to 8 such as oxalic acid; malonic acid; succinic acid; glutaric acid; adipic acid; pimelic acid; suberic acid; azelaic acid; sebacic acid;

(d) hydroxyalkyl carboxylic acids such as citric acid; tartaric acids; malic acid; mandelic acid; and 12-hydroxystearic acid;

(e) unsaturated alkyl carboxylic acids such as maleic acid; fumaric acid; and cinnamic acid;

(f) fused ring aromatic carboxylic acids such as naphthalenic acid; and anthracene carboxylic acid; and (g) cycloaliphatic acids such as cyclohexane carboxylic acid; cyclopentane carboxylic acid; furan carboxylic acids.

(2) Organic sulfur acids including:

(a) sulfonic acids including:

(1) benzenesulfonic acids such as benzenesulfonic acid; phenolsulfonic acid; dodecylbenzenesulfonic acid; benzenedisulfonic acid, benzenetrisulfonic acids; para-toluenesulfonic acid;

(2) alkyl sulfonic acids such as methane sulfonic acid; ethane sulfonic acid; butane sulfonic acid; butane disulfonic acid; sulfosuccinate alkyl esters such as dioctyl succinyl sulfonic acid; and alkyl polyethoxy-succinyl sulfonic acid.

(b) alkyl sulfates such as the lauryl half ester of sulfuric acid and the octadecyl half ester of sulfuric acid.

(3) Organophosphorus acids including:

(a) phosphonic acids having the formula:

wherein R is an aryl group or alkyl having 1 to 22 carbon atoms;

(b) phosphinic acids having the formula:

wherein R is an aryl group or alkyl group having 1 to 22 carbon atoms such as dicyclohexyl phosphinic acid; dibutyl phosphinic acid; and dilauryl phosphinic acid;

(c) thiophosphinic acids having the formula:

wherein R is an aryl group or alkyl group having 1 to 22 carbon atoms such as di-iso-butyl dithiophosphinic acid; dibutyl dithiophosphinic acid; dioctadecyl dithiophosphinic acid;

(d) phosphites, that is diesters of phosphorous acid having the formula: HO—P (OR)$_2$ wherein R is an alkyl group having 1 to 22 carbon atoms such as dioctadecylphosphite; and (e) phosphates, that is diesters of phosphoric acid having the formula:

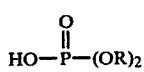

wherein R is an alkyl group having 1 to 22 carbon atoms, such as dioctadecyl phosphate.

(4) Phenols such as phenol; hydroquinone; t-butylcatechol; p-methoxyphenol; and naphthols.

(5) thioacids having the formula:

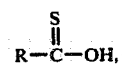

and

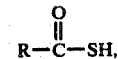

and

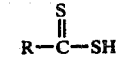

wherein R is an aryl group or alkyl group having 1 to 22 carbon atoms, such as thiosalicylic acid; thiobenzoic acid; thioacetic acid; thiolauric acid; and thiostearic acid.

(6) Amino acids such as the naturally occurring amino acids and derivatives thereof such as 6-aminohexanoic acid; 12-aminododecanoic acid; N-phenylglycine; and 3-aminocrotonic acid.

(7) Polymeric acids prepared from acidic monomers wherein the acidic function remains in the polymer chain such as low molecular weight acrylic acid polymers and copolymers; and styrene-maleic anhydride copolymers.

(8) Miscellaneous acids and acid salts such as ferrocyanide; ferricyanide; sodium tetraphenylborate; phosphotungstic acid; phosphosilicic acid, or any other such anion which will form a tight ion pair with an organic cation, i.e., any such anion which forms a water insoluble precipitate with an organic cation.

The clays used to prepare the organophilic clay gellants of this invention are smectite-type clays which have a cation exchange capacity of at least 75 milliequivalents per 100 grams of clay. Particularly desirable types of clay are the naturally-occurring Wyoming varieties of swelling bentonites and like clays and hectorite, a swelling magnesium-lithium silicate clay.

The clays, especially the bentonite type clays, are preferably converted to the sodium form if they are not already in this form. This can conveniently be done by preparing an aqueous clay slurry and passing the slurry through a bed of cation exchange resin in the sodium form. Alternatively, the clay can be mixed with water and a soluble sodium compound such as sodium carbonate, sodium hydroxide and the like, followed by shearing the mixture with a pugmill or extruder.

Smectite-type clays occur naturally or may be prepared synthetically by either a pneumatolytic or hydrothermal synthesis processes. Representative of such clays are montmorillonite, bentonite, beidellite, hectorite, saponite, and stevensite. The cation exchange capacity of the smectite-type clays can be determined by the well-known ammonium acetate method.

The organophilic clays of this invention can be prepared by admixing the clay, organic cation, organic anion and water together, preferably at a temperature within the range from 20° C. to 100° C., more preferably 35° C. to 77° C. for a period of time sufficient for the organic cation and organic anion complex to intercalate with the clay particles, followed by filtering, washing, drying and grinding.

The compositions of the invention as discussed above find wide utility as rheological additives in non-aqueous fluid systems generally.

The non-aqueous fluid compositions in which the self activating organophilic clays are useful include paints, varnishes, enamels, waxes, epoxies, mastics, adhesives, cosmetics, inks, polyester laminating resins and polyester gel coats, and the like. These fluids may be prepared by any conventional method such as described in U.S. Pat. No. 4,208,218 including colloid mills, roller mills, ball mills, and high speed dispersers in which the pigment materials become well dispersed in the organic vehicle by the high shear used in processing.

The organophilic clay gellant is employed in such compositions in amounts sufficient to obtain the desired rheological properties such as high viscosity at low shear rates, control of sagging of fluid films and prevention of settling and hard packing of pigments present in the non-aqueous fluid compositions. Amounts of the organophilic clay gellant employed in the non-aqueous fluid system should preferably be between about 0.1% and about 15% based on the weight of the treated non-aqueous fluid system and preferably between 0.3% and 5.0% to yield the desired rheological effects.

The following examples are given to illustrate the invention, but are not deemed to be limiting thereof. All percentages given throughout the specification are based upon weight unless otherwise indicated.

A simple convenient test has been devised to illustrate the enhanced dispersion characteristics of the organophilic clays utilized in this invention and exemplified in the following Examples to show the results potentially obtainable in utilizing the compositions of this invention. The test is called the solvent compatibility test. The solvent compatibility test is conducted by taking a sample of the organophilic clay which is sifted into 10 milliliters of various solvents contained in separate 10 milliliter graduated cylinders. The organophilic clay is added at such a rate that the particles are wetted evenly and clumping is not permitted to occur. The samples are allowed to equilibrate after all the organophilic clay has been added (approximately 30 minutes). The volume occupied by the organophilic clay is then recorded in tenths of a milliliter; this number is called the swelling volume.

The mixture is vigorously shaken 50 times, 10 times horizontally, 40 times vertically, and allowed to stand overnight. The volume occupied by the organophilic clay is again recorded in tenths of a milliliter; this value is called the settling volume.

The swelling volume gives an indication of the compatibility of the organic portion of the organophilic clay with the solvents tested; the settling volume gives an indication of the ease of dispersion of the organophilic clay in that solvent under low shear conditions.

Because of variances in the rate of sifting of the organoclay into the solvent and the vigor with which the sample is shaken, the numbers are not absolute. Small differences in the volumes are not considered significant, rather, the values are intended to be for comparison only.

The inventive organophilic clay gellants employed in the examples were prepared by the following procedure, unless otherwise noted. A 3% clay slurry (sodium form of Wyoming bentonite) and the slurry was heated to 60° C. with stirring. The organic anion was added to the clay slurry and reacted for approximately 10 minutes followed by addition of the organic cation. The amounts or organic materials added are set forth in the Tables and expressed in milliequivalents of the organic cation and organic anion per 100 g of clay, 100% active clay basis. The mixture was then reacted under agitation for a period of time sufficient to complete the reaction (generally 10 to 60 minutes). The organoclay is collected on a vacuum filter. The filter cake is washed with hot (40°-80° C.) water and dried at 60° C. The dried organoclay is ground using a hammer mill or similar grinding apparatus to reduce the particle size and then sieved through a 200-mesh screen.

EXAMPLE 1

Allyl methyl di(hydrogenated-tallow) ammonium chloride (abbreviated AM2HT).

Placed 824.7 gm. methyl di(hydrogenated-tallow) amine, approximately 350 ml. isopropyl alcohol, 250 gm. $NaHCO_3$, 191.3 gm. allyl chloride, and 10 gm. allyl bromide (as a catalyst) in a 4-liter reaction vessel equipped with a condenser and mechanical stirrer. The mixture was heated and allowed to reflux gently. Periodically, samples were removed, filtered, and titrated with standardized HCl and NaOH. The reaction was considered complete when there was 0.0% amine HCl and 1.8% amine. The final analysis showed an effective gram molecular weight of 831.17.

EXAMPLES 2-4

A 3% clay slurry, the sodium form of Wyoming bentonite in Examples 2 and 3 and hectorite in Example 4, was heated to 60° C. with stirring. A solution of organic cationic compound, ethanol methyl di(hydrogenated-tallow) ammonium chloride [EM2HT], for Example 2, and AM2HT prepared in Example 1 for examples 3 and 4, was added to the clay slurry and stirred for 20 minutes. The organoclay was collected on a vacuum filter. The filter cake was washed with 60° C. water and dried at 60° C. The dried organoclay was ground using a hammer mill to reduce the particle size and then sieved through a U.S. Standard 200 mesh screen.

EXAMPLES 5-24

These examples demonstrate the preparation of organophilic clays of this invention using various organic anions and allyl methyl di(hydrogenated-tallow) ammonium chloride (AM2HT) as the organic cation. A conventional organophilic clay using AM2HT as the organic cation is presented as a comparative example. The compositions are set forth in Table I with the solvent compatibility results in Table I(a). The data illustrates the superior dispersion characteristics of the inventive organophilic clays as compared with organophilic clays prepared in the absence of the organic anion.

TABLE I

| Example No. | Organic Anion (Salt) | Organic Anion M.E. Ratio | Organic Cation M.E. Ratio |
|---|---|---|---|
| 5 | Na Benzoate | 15 | 115 |
| 6 | Na Benzoate | 22.5 | 122.5 |
| 7 | Na Benzoate | 30 | 130 |
| 8 | Na Benzoate | 10 | 110 |
| 9 | Na Benzoate | 22.5 | 130 |
| 10 | Na p-Phenolsulfonate | 15 | 115 |
| 11 | Na p-Phenolsulfonate | 30 | 130 |
| 12 | Na p-Phenolsulfonate | 22.5 | 122.5 |
| 13 | Na p-Phenolsulfonate | 10 | 110 |
| 14 | Na Salicylate | 30 | 130 |
| 15 | Na Salicylate | 22.5 | 122.5 |
| 16 | Na Salicylate | 15 | 115 |
| 17 | Na Dioctadecyl Phosphite | 22.5 | 122.5 |
| 18 | Benzoic Acid | 22.5 | 122.5 |

TABLE I-continued

| Example No. | Organic Anion (Salt) | Organic Anion M.E. Ratio | Organic Cation M.E. Ratio |
|---|---|---|---|
| 19 | Disodium Phthalate | 22.5 | 122.5 |
| 20 | Na Octoate | 22.5 | 122.5 |
| 21 | Na Stearate | 22.5 | 122.5 |
| 22 | Na Laurate | 22.5 | 122.5 |
| 23 | Na 12-Hydroxystearate | 22.5 | 122.5 |
| 24 | Na$_3$ Citrate | 22.5 | 122.5 |
| Comparative | None | None | 114 |

TABLE II

| Example No. | Organic Anion (Salt) | Organic Anion M.E. Ratio | Organic Cation M.E. Ratio |
|---|---|---|---|
| 25 | Na Salicylate | 22.5 | 129.4 |
| 26 | Na Napthalene-1-Carboxylate | 22.5 | 129.4 |
| 27 | Na p-Toluate | 22.5 | 122.5 |
| 28 | Na Borate | 22.5 | 122.5 |
| 29 | Disodium Phthalate | 22.5 | 122.5 |
| 30 | Na Benzoate | 22.5 | 129.4 |
| 31 | Na Ferricyanide | 22.5 | 122.5 |
| 32 | Na Tetraphenylborate | 22.5 | 122.5 |
| 33 | Na 1-Butanesulfonate | 22.5 | 122.5 |
| 34 | Na p-Toluenesulfonate | 22.5 | 122.5 |
| 35 | Na Benzenesulfonate | 22.5 | 122.5 |
| 36 | Na Benzene-1,3-sulfonate | 22.5 | 122.5 |
| 37 | Na p-Phenolsulfonate | 22.5 | 122.5 |
| 38 | Na 12-Hydroxystearate | 22.5 | 122.5 |
| 39 | Na Oleate | 22.5 | 122.5 |
| 40 | Na Stearate | 22.5 | 122.5 |
| 41 | Na Laurate | 22.5 | 122.5 |
| 42 | Na Octoate | 22.5 | 122.5 |
| 43 | Na 2-Ethylhexanoate | 22.5 | 122.5 |
| 44 | Na Hexanoate | 22.5 | 122.5 |
| 45 | Na Dodecylbenzenesulfonate | 22.5 | 122.5 |
| Comparative | None | None | 110 |

TABLE I (a)

Solvent Compatibility

| Example No. | Toluene Swelling Volume | Toluene Settling Volume | Methyl isobutyl ketone Swelling Volume | Methyl isobutyl ketone Settling Volume | 60/40 Di-isodecyl Phthalate/Toluene Swelling Volume | 60/40 Di-isodecyl Phthalate/Toluene Settling Volume | Heptane Swelling Volume | Heptane Settling Volume |
|---|---|---|---|---|---|---|---|---|
| 5 | 10 | 100 | 12 | 19 | 10 | 8 | 18 | 27 |
| 6 | 10 | 100 | 11 | 18 | 8 | 10 | 28 | 33 |
| 7 | 15 | 100 | 11 | 17 | 8 | 8 | 28 | 42 |
| 8 | 8 | 76 | 10 | 20 | 7 | 8 | 10 | 12 |
| 9 | 8 | 80 | 14 | 20 | 10 | 10 | 30 | 44 |
| 10 | 12 | 78 | 13 | 16 | 11 | 14 | 14 | 18 |
| 11 | 12 | 48 | 12 | 18 | 8 | 10 | 22 | 68 |
| 12 | 8 | 100 | 12 | 14 | 10 | 12 | 27 | 32 |
| 13 | 12 | 68 | 13 | 17 | 10 | 11 | 9 | 12 |
| 14 | 16 | 100 | 14 | 19 | 10 | 14 | 26 | 34 |
| 15 | 11 | 100 | 12 | 18 | 9 | 10 | 23 | 29 |
| 16 | 12 | 100 | 12 | 17 | 9 | 9 | 16 | 22 |
| 17 | 7 | 100 | 12 | 16 | 10 | 5 | 20 | 26 |
| 18 | 8 | 32 | 13 | 17 | 7 | 8 | 22 | 70 |
| 19 | 10 | 100 | 14 | 18 | 9 | 8 | 20 | 52 |
| 20 | 12 | 36 | 14 | 20 | 7 | 8 | 32 | 57 |
| 21 | 11 | 100 | 13 | 19 | 8 | 11 | 58 | 44 |
| 22 | 12 | 100 | 13 | 17 | 8 | 9 | 32 | 37 |
| 23 | 14 | 100 | 12 | 18 | 10 | 10 | 37 | 44 |
| 24 | 10 | 100 | 12 | 20 | 10 | 11 | 34 | 52 |
| Comparative | 15 | 88 | 13 | 16 | 16 | 20 | 7 | 11 |

EXAMPLES 24-25

These examples demonstrate the preparations of organophilic clays of this invention using various organic anions and diallyl di(hydrogenated tallow) ammonium chloride as (2A2HT) organic cation. A conventional organophilic clay using 2A2HT as the organic cation is presented as a comparative example. The compositions are set forth in Table II with the solvent compatibility results in Table II(a). The data illustrates the much superior dispersion characteristics of the inventive organophilic clays as compared with organophilic clays prepared in the absence of the organic anion.

TABLE II (a)

Solvent Compatibility

| Example No. | Toluene Swelling Volume | Toluene Settling Volume | Methyl isobutyl ketone Swelling Volume | Methyl isobutyl ketone Settling Volume | 60/40 Di-isodecyl Phthalate/Toluene Swelling Volume | 60/40 Di-isodecyl Phthalate/Toluene Settling Volume | Lacquer Solvent Swelling Volume | Lacquer Solvent Settling Volume |
|---|---|---|---|---|---|---|---|---|
| 25 | | 34 | | 18 | | 12 | | 26 |
| 26 | 14 | 37 | 12 | 16 | 13 | 13 | 14 | 80 |
| 27 | 13 | 28 | 12 | 16 | 10 | 12 | 14 | 23 |
| 28 | 10 | 57 | 11 | 17 | 11 | 10 | 16 | 100 |
| 29 | 15 | 37 | 12 | 18 | 12 | 11 | 16 | 22 |
| 30 | | 54 | | 18 | | 13 | | 87 |
| 31 | 9 | 53 | 11 | 16 | 10 | 13 | 18 | 33 |
| 32 | 10 | 5 | 11 | 14 | 9 | 10 | — | — |
| 33 | 12 | 73 | 10 | 12 | 10 | 12 | 15 | 88 |
| 34 | 13 | 18 | 11 | 14 | 11 | 12 | 14 | 82 |
| 35 | 12 | 16 | 12 | 14 | 10 | 12 | 16 | 88 |

TABLE II (a)-continued

| | Solvent Compatibility Solvent | | | | | | | |
|---|---|---|---|---|---|---|---|---|
| | Toluene | | Methyl isobutyl ketone | | 60/40 Di-isodecyl Phthalate/Toluene | | Lacquer Solvent | |
| Example No. | Swelling Volume | Settling Volume | Swelling Volume | Settling Volume | Swelling Volume | Settling Volume | Swelling Volume | Settling Volume |
| 36 | 14 | 38 | 12 | 15 | 12 | 13 | 14 | 22 |
| 37 | 14 | 45 | 12 | 11 | 12 | 12 | 14 | 80 |
| 38 | 14 | 46 | 12 | 14 | 10 | 14 | 16 | 84 |
| 39 | 16 | 30 | 12 | 18 | 12 | 12 | 14 | 78 |
| 40 | 14 | 100 | 18 | 32 | 16 | 90 | 18 | 94 |
| 41 | 14 | 32 | 12 | 18 | 10 | 10 | 16 | 80 |
| 42 | 14 | 52 | 12 | 20 | 12 | 14 | 16 | 100 |
| 43 | 14 | 64 | 10 | 16 | 10 | 12 | 15 | 80 |
| 44 | 10 | 54 | 12 | 20 | 10 | 14 | 17 | 82 |
| 45 | 12 | 12 | 12 | 13 | 9 | 10 | 12 | 50 |
| Comparative | 14 | 33 | 12 | 14 | 12 | 15 | 16 | 22 |

EXAMPLES 46-58

These examples demonstrate the preparations of organophilic clays of this invention using various organic anions and ethanol dimethyl hydrogenated tallow ammonium chloride (E2MHT) as the organic cation. A conventional organophilic clay using E2MHT as the organic cation is presented as a comparative example. The compositions are set forth in Table III with the solvent compatibility results in Table III(a). The data illustrates the much superior dispersion characteristics of the inventive organophilic clays as compared with organophilic clays prepared in the absence of the organic anion.

TABLE III

| Example No. | Organic Anion (Salt) | Organic Anion M.E. Ratio | Organic Cation M.E. Ratio |
|---|---|---|---|
| 46 | Na Benzoate | 22.5 | 114 |
| 47 | Na Benzoate | 30 | 130 |
| 48 | Na Benzoate | 22.5 | 122.5 |
| 49 | Na Phenolate | 22.5 | 122.5 |
| 50 | Na Tetraphenylborate | 22.5 | 122.5 |
| 51 | Na Ferrocyanide | 22.5 | 122.5 |
| 52 | Na Fluorescein Derivative | 22.5 | 122.5 |
| 53 | Rose Bengal | 22.5 | 122.5 |
| 54 | Disodium Phthalate | 22.5 | 122.5 |
| 55 | Na Laurate | 22.5 | 122.5 |
| 56 | Na Octoate | 22.5 | 122.5 |
| 57 | Na Stearate | 22.5 | 122.5 |
| 58 | Na Abietate | 22.5 | 122.5 |
| Comparative | None | None | 108.1 |

| | Toluene | | Methyl isobutyl ketone | | 60/40 Di-isodecyl Phthalate/Toluene | | Heptane | |
|---|---|---|---|---|---|---|---|---|
| Example No. | Swelling Volume | Settling Volume | Swelling Volume | Settling Volume | Swelling Volume | Settling Volume | Swelling Volume | Settling Volume |
| 46 | 13 | 18 | | 24 | 10 | 12 | 16 | 18 |
| 47 | 20 | 46 | 19 | 29 | 14 | 16 | 20 | 32 |
| 48 | 14 | 22 | 20 | 26 | 14 | 14 | 16 | 24 |
| 49 | 18 | 28 | 18 | 26 | 14 | 15 | 20 | 28 |
| 50 | 12 | 22 | 18 | 30 | 13 | 15 | 20 | 28 |
| 51 | 14 | 26 | 22 | 38 | 9 | 10 | 17 | 26 |
| 52 | 16 | 30 | 19 | 28 | 10 | 13 | 21 | 30 |
| 53 | 16 | 26 | 21 | 27 | 11 | 12 | 22 | 28 |
| 54 | 18 | 36 | 22 | 30 | 18 | 21 | — | — |
| 55 | 16 | 33 | 18 | 26 | 14 | 18 | — | — |
| 56 | 17 | 30 | 22 | 28 | 14 | 18 | — | — |
| 57 | 17 | 24 | 12 | 16 | 10 | 12 | — | — |
| 58 | 17 | 30 | 23 | 32 | 12 | 12 | — | — |
| Comparative | 6 | 8 | 17 | 19 | 8 | 10 | 12 | 14 |

EXAMPLES 59-72

These examples demonstrate the preparations of organophilic clays of this invention using various organic anions and various quaternary ammonium chlorides as the organic cation. A conventional organophilic clay using ethanol methyl di(hydrogenated tallow) as the organic cation is presented as a comparative example. The compositions are set forth in Table IV with the solvent compatibility results in Table IV(a). The data illustrates the much superior dispersion characteristics of the inventive organophilic clays as compared with organophilic clays prepared in the absence of the organic anion.

TABLE IV

| Example No. | Organic Cation | Organic Anion | Organic Cation M.E. Ratio | Organic Anion M.E. Ratio |
| --- | --- | --- | --- | --- |
| 59 | Allyl Dimethyl Hydrogenated Tallow | Na₂ Phthalate | 122.5 | 22.5 |
| 60 | Allyl Dimethyl Hydrogenated Tallow | Na Octoate | 122.5 | 22.5 |
| 61 | Allyl Dimethyl Hydrogenated Tallow | Na Laurate | 122.5 | 22.5 |
| 62 | Allyl Dimethyl Hydrogenated Tallow | Na Stearate | 122.5 | 22.5 |
| 63 | Allyl Dimethyl Hydrogenated Tallow | Na Abietate | 122.5 | 22.5 |
| 64 | Ethanol Methyl Di(Hydrogenated Tallow) | Na Benzoate | 130 | 30 |
| 65 | Ethanol Methyl Di(Hydrogenated Tallow) | Na 9,10-Epoxystearate | 122.5 | 22.5 |
| 66 | Ethanol Methyl Di(Hydrogenated Tallow) | Na Dioctadecyl Phosphite | 122.5 | 22.5 |
| 67 | Ethanol Methyl Di(Hydrogenated Tallow) | Na Oleate | 122.5 | 22.5 |
| 68 | Diallyl Methyl Octadecyl | Na₂ Phthalate | 122.5 | 22.5 |
| 69 | Triallyl Hydrogenated Tallow | Na₂ Phthalate | 122.5 | 22.5 |
| 70 | Triethanol Hydrogenated Tallow | Na₂ Phthalate | 122.5 | 22.5 |
| 71 | Triethanol Hydrogenated Tallow | Na Benzoate | 122.5 | 22.5 |
| 72 | Triethanol Hydrogenated Tallow | Na Benzoate | 115 | 15 |
| Comparative | Ethanol Methyl Di(Hydrogenated Tallow) | None | 108.2 | None |

TABLE IV (a)

| | Solvent Compatibility | | | | | | | |
| --- | --- | --- | --- | --- | --- | --- | --- | --- |
| | Solvent | | | | | | | |
| | Toluene | | Methyl isobutyl ketone | | 60/40 Di-isodecyl Phthalate/Toluene | | Heptane | |
| Example No. | Swelling Volume | Settling Volume | Swelling Volume | Settling Volume | Swelling Volume | Settling Volume | Swelling Volume | Settling Volume |
| 59 | 15 | 46 | 14 | 21 | 14 | 13 | 13 | 20 |
| 60 | 20 | 80 | 16 | 32 | 18 | 10 | 24 | 100 |
| 61 | 16 | 78 | 18 | 42 | 16 | 10 | 24 | 100 |
| 62 | 18 | 78 | 24 | 38 | 17 | 10 | 24 | 100 |
| 63 | 19 | 78 | 14 | 40 | 16 | 10 | 24 | 100 |
| 64 | 8 | 72 | 10 | 12 | 9 | 8 | 10 | 12 |
| 65 | 18 | 50 | 12 | 18 | 14 | 14 | — | — |
| 66 | 12 | 84 | 14 | 81 | 18 | 18 | — | — |
| 67 | 14 | 20 | 16 | 26 | 12 | 16 | — | — |
| 68 | 13 | 51 | 28 | 94 | 22 | 42 | 25 | 51 |
| 69 | 16 | 31 | 14 | 20 | 14 | 15 | 12 | 17 |
| 70 | 12 | 22 | 12 | 22 | 11 | 13 | 14 | 20 |
| 71 | 12 | 25 | 13 | 26 | 12 | 14 | 14 | 26 |
| 72 | 11 | 15 | 16 | 20 | 11 | 12 | 13 | 16 |
| Comparative | 12 | 18 | 12 | 14 | 11 | 14 | 14 | 16 |

EXAMPLES 73-79

These examples demonstrate the preparations of organophilic clays of this invention using various organic anions and diethanol methyl hydrogenated tallow ammonium chloride (2EMHT) as the organic cation. A conventional organophilic clay using 2EMHT as the organic cation is presented as a comparative example. The compositions are set forth in Table V with the solvent compatibility results in Table V(a). The data illustrates the much superior dispersion characteristics of the inventive organophilic clays as compared with organophilic clays prepared in the absence of the organic anion.

TABLE V

| Example No. | Organic Anion (Salt) | Organic Anion M.E. Ratio | Organic Cation M.E. Ratio |
| --- | --- | --- | --- |
| 73 | Na Benzoate | 15 | 115 |
| 74 | Na Benzoate | 15 | 122.5 |
| 75 | Na₂ Phthalate | 22.5 | 122.5 |
| 76 | Na Octoate | 22.5 | 122.5 |
| 77 | Na Laurate | 22.5 | 122.5 |
| 78 | Na Stearate | 22.5 | 122.5 |
| 79 | Na Abietate | 22.5 | 122.5 |
| Comparative | None | None | 111.7 |

TABLE V (a)

| | Solvent Compatibility | | | | | | | |
| --- | --- | --- | --- | --- | --- | --- | --- | --- |
| | Solvent | | | | | | | |
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| 73 | 8 | 10 | 22 | 26 | 8 | 9 | 16 | 20 |
| 74 | 9 | 14 | 15 | 35 | 10 | 12 | 16 | 24 |
| 75 | 10 | 12 | 18 | 20 | 10 | 10 | 16 | 17 |
| 76 | 10 | 14 | 18 | 26 | 8 | 10 | — | — |
| 77 | 9 | 12 | 18 | 26 | 8 | 9 | — | — |
| 78 | 3 | 3 | 12 | 12 | 4 | 4 | — | — |
| 79 | 5 | 5 | 27 | 32 | 2 | 2 | — | — |

TABLE V (a)-continued

| | Solvent Compatibility Solvent | | | | | | | |
| --- | --- | --- | --- | --- | --- | --- | --- | --- |
| | Toluene | | Methyl isobutyl ketone | | 60/40 Di-isodecyl Phthalate/Toluene | | n-Butyl Acetate | |
| Example No. | Swelling Volume | Settling Volume | Swelling Volume | Settling Volume | Swelling Volume | Settling Volume | Swelling Volume | Settling Volume |
| Comparative | 4 | 4 | 19 | 22 | 5 | 8 | 14 | 17 |

The invention being thus described, it will be obvious that the same may be varied in many ways. Such variations are not to be regarded as a departure from the spirit and scope of the invention and all such modifications are intended to be included within the scope of the following claims.

We claim:

1. An organophilic clay gellant comprising the reaction product of:
   a. a smectite-type clay having a cation exchange capacity of at least 75 milliequivalents per 100 grams of said clay;
   b. an organic anion in an amount ranging from 5 to 100 milliequivalents per 100 grams of said smectite-type clay, 100% active clay basis; and
   c. an organic cation having the formula

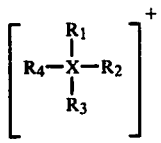

wherein $R_1$ is selected from the group consisting of a $\beta,\gamma$-unsaturated alkyl group having less than 7 aliphatic carbon atoms, a hydroxyalkyl group having 2 to 6 aliphatic carbon atoms and mixtures thereof, $R_2$ is a long chain alkyl group having 12 to 60 carbon atoms, $R_3$ and $R_4$ are individually selected from the group consisting of a $\beta,\gamma$-unsaturated alkyl group having less than 7 aliphatic carbon atoms, a hydroxyalkyl group having 2 to 6 carbon atoms, an aralkyl group having 1 to 22 carbon atoms in the alkyl portion, an alkyl group having from 1 to 22 carbon atoms and mixtures thereof and X is selected from the group consisting of phosphorous and nitrogen, said organic cation being present in an amount sufficient to at least satisfy the cation exchange capacity of the smectite-type clay and the cationic activity of the organic anion, wherein the cation exchange sites of the smectite-type clay are substituted with the organic cation and wherein an organic cation-organic anion complex is intercalated with the clay.

2. The gellant of claim 1, wherein the $\beta,\gamma$-unsaturated alkyl group is selected from a group consisting of cyclic groups, acyclic alkyl groups having less than 7 carbon atoms, acyclic alkyl groups substituted with aromatic groups, and aromatic groups substituted with aliphatic groups.

3. The gellant of claim 1 wherein the hydroxyalkyl group is selected from a group consisting of cyclic groups and aliphatic groups having 2 to 6 carbon atoms with the hydroxy substitution on $C_2$ to $C_6$.

4. The gellant of claim 2 wherein $R_2$ has from 12 to 22 carbon atoms.

5. The gellant of claim 4 wherein $R_2$ is along chain fatty acid group.

6. The gellant of claim 1 wherein the organic anion is derived from an organic acid having a $pK_A$ less than about 11.0.

7. The gellant of claim 1 wherein the smectite-type clay is selected from the group consisting of hectorite and sodium bentonite.

8. The gellant of claim 1 wherein the amount of said organic cation is from 80 to 200 milliequivalents per 100 grams of clay, 100% active clay basis.

9. The gellant of claim 1 wherein the amount of said organic cation is from 100 to 160 milliequivalents per 100 grams of clay, 100% active clay basis.

10. A process for preparing an organophilic clay gellant which comprises:
    a. preparing an aqueous slurry of smectite-type clay having a cation exchange capacity of at least 75 milliequivalents per 100 grams of clay, said clay ranging from about 1 to about 80% by weight of slurry;
    b. heating the slurry to a temperature between 20° C. and 100° C.;
    c. adding from about 5 to 100 milliequivalents of an organic anion per 100 grams of clay, 100% active clay basis and an organic cation compound, wherein said organic cation has the formula:

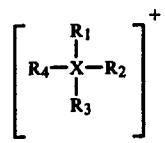

wherein $R_1$ is selected from the group consisting of a $\beta,\gamma$-unsaturated alkyl group having less than 7 aliphatic carbon atoms, a hydroxyalkyl group having 2 to 6 aliphatic carbon atoms, and mixtures thereof; $R_2$ is a long chain alkyl group having 12 to 60 carbon atoms; $R_3$ and $R_4$ are individually selected from the group consisting of a $\beta,\gamma$-unsaturated alkyl group having less than 7 aliphatic carbon atoms, a hydroxyalkyl group having 2 to 6 aliphatic carbon atoms, an aralkyl group having 1 to 22 carbon atoms in the alkyl portion, an alkyl group having from 1 to 22 carbon atoms and mixtures thereof; X is selected from a group consisting of phosphorous and nitrogen; said organic cation compound is used in a sufficient amount to at least satisfy the cation exchange capacity of the smectite-type clay and the cationic activity of the organic anion while agitating the reaction solution; and d. reacting the mixture for a sufficient time to form a reaction product comprising an organic cation-organic anion complex which is intercalated with the smectite-type clay and the cation exchange sites of the smectite-type clay are substituted with the organic cation.

11. The process of claim 10 wherein the organic cation is selected from the group consisting of quaternary ammonium salts and phosphonium salts containing at least one lineal or branched alkyl group having 12 to 22 carbon atoms.

12. The process of claim 10 wherein the organic anion is derived from an organic acid having a $pK_A$ less than about 11.0.

13. The process of claim 10 wherein the smectite-type clay is selected from the group consisting of hectorite and sodium bentonite.

14. The process of claim 10 wherein the amount of said organic anion is from 10 to 50 milliequivalents per 100 grams of said clay, 100% active clay basis.

15. The process of claim 10 wherein the amount of said organic cation compound is from 80 to 200 milliequivalents per 100 grams of clay, 100% active clay basis.

16. The process of claim 10 wherein the organic anion is added to the smectite-type clay prior to the addition of the organic cation compound.

17. The process of claim 10 wherein the organic anion and organic cation compound are added to the smectite-type clay in the form of an organic cation-organic anion complex.

* * * * *